United States Patent [19]

Chapman et al.

[11] 4,231,256

[45] Nov. 4, 1980

[54] THERMOELECTRIC GAS DRYER

[75] Inventors: Robert L. Chapman, La Habra; John N. Harman, III, Placentia, both of Calif.

[73] Assignee: Beckman Instruments, Inc., Fullerton, Calif.

[21] Appl. No.: 9,203

[22] Filed: Feb. 5, 1979

[51] Int. Cl.³ ............................................. G01N 1/22
[52] U.S. Cl. ................................... 73/421.5 R; 62/3; 62/281
[58] Field of Search .................. 73/421.5 A, 421.5 R; 62/3, 55.5, 281; 55/267, 355, 35; 422/101; 137/171, 183, 204

[56] References Cited

U.S. PATENT DOCUMENTS

| | | | |
|---|---|---|---|
| 2,687,342 | 8/1954 | Strange et al. | 23/232 |
| 3,148,532 | 9/1964 | Broerman | 62/3 |
| 3,176,501 | 4/1965 | Briggs | 73/23.1 |
| 3,309,843 | 3/1967 | Rigopulos | 55/35 |
| 3,367,120 | 2/1968 | Franklin | 62/3 |
| 3,407,646 | 10/1968 | Traver | 73/23 |
| 3,557,869 | 1/1971 | Kriftel | 62/281 |
| 3,567,394 | 3/1971 | Betz | 23/254 |
| 3,581,469 | 6/1971 | Davis | 55/126 |
| 3,593,023 | 7/1971 | Dodson | 250/43.5 |
| 3,771,960 | 11/1973 | Kim | 23/232 |
| 3,822,581 | 7/1974 | Hauk | 73/23 |

Primary Examiner—S. Clement Swisher
Attorney, Agent, or Firm—Robert J. Steinmeyer; Paul R. Harder; Frank J. Kowalski

[57] ABSTRACT

A method and apparatus for removing moisture from a sample stream of gas while preventing dilution of the concentration of components of successive increments of the sample stream of gas.

17 Claims, 5 Drawing Figures

THERMOELECTRIC GAS DRYER

BACKGROUND OF THE INVENTION

The present invention pertains to a method and apparatus for drying a sample stream of gas and more particularly to a new and useful method and apparatus for removing the condensate from a gas stream while minimally interfering with the flow of the sample stream.

Presently, gas analyzers have instantaneous measurement of component concentration capabilities. However, in some applications, such as the measurement of component concentration in automobile exhaust gas, the instantaneous analysis capability is defeated by its moisture content. Although the analyzer can respond instantaneously to concentration changes, the moisture in the sample stream of exhaust gas must be removed in order to permit an accurate analysis of the component concentration. Prior art gas dryers have a significant deficiency in this area. Referring to FIG. 1, it can be seen that the gas concentration at 5 is significantly different from the concentration at 6 corresponding to the inlet and outlet of a volume 9 used for removing moisture from a sample stream of gas. As illustrated in FIG. 1, prior art condensate removal systems have an intake 7 and exhaust 8 with a large volume 9 therebetween. This large volume causes a mixing or integrating between the sample arriving at intake 7 and the sample contained in the volume used in cooling the sample gas. As a result, the concentration at exhaust 8 will not immediately represent the concentration at intake 7 but will initially represent the concentration in volume 9, then represent the mixture of the concentration in volume 9 plus the concentration at intake 7, and finally represent the concentration at intake 7. This process can best be seen through a comparison of curve 2A and 2B of FIG. 2. Curve 2A represents the concentration of a gas to be measured at intake 7 with respect to time. Curve 2B represents the concentration of the same gas at exhaust 8 with respect to time for the same time period. Since both concentrations are measured on the same time scale, it can easily be seen that a time delay X occurs between the reduction of concentration at intake 7 and a significant decrease in the measured concentration at exhaust 8. Should a second pulsed increase in concentration occur before the concentration at exhaust 8 decreases to its minimum, curve 2B will begin to increase and an accurate measurement of the concentration minimum is lost. Loss of accurate measurement will also occur when the concentration increases to an extremely high maximum for a short duration (spiking) and continue at a low value thereafter.

The problem of missing the maximums and minimums of a component gas concentration in a sample gas stream is particularly critical in the automobile exhaust testing area. The carburetor balance of an automobile engine is indicated by the various concentrations of carbon dioxide and oxygen in the exhaust stream. When a particular cylinder is misfiring, a radical change in the oxygen concentration in the exhaust will occur. While the component concentration measurement device is capable of sensing this radical change in concentration when it is used by itself, the combination of the measurement device with a prior art gas dryer greatly reduces sensitivity as illustrated in FIG. 2.

SUMMARY OF THE INVENTION

The present invention eliminates the problems of prior art moisture removal systems through the use of a design which combines a solid state cooling device, a peltier block, in conjunction with gravity moisture separation housing having a wick to produce "plugged flow" and to draw the moisture out of the housing. A solid state cooling block is used with a temperature dependent current control device to reduce the temperature of the gas sample, thus instantaneously compensating for temperature changes in the sample gas stream and promoting condensation of any moisture which may be contained within the sample. The condensate is separated from the gas sample through gravity and settles to the bottom of the housing. The housing has three intersecting paths. One of the three paths receives the flow of a sample gas stream. A second path exhausts the sample stream. The third path has a hygroscopic wick disposed therein to draw moisture from the intersection point of the first two paths, partially through gravity, partially through the pressure of the flow of the sample stream and partially through the hygroscopic nature of the wick material. This hygroscopic wick will prevent the exhaust of the sample gas through the third path so that "plugged flow" is achieved. By providing fast, efficient cooling through the use of a solid state cooling device, the length and cross sectional area of passages for sample gas flow may be reduced. Through plugged flow, the sample gas travels quickly from inlet to outlet. Thus, no intermixing of successive increments of the sample gas stream take place and increased accuracy in instantaneous component concentration gas analysis is possible.

DESCRIPTION OF THE PREFERRED EMBODIMENT

Figures 3, 4:
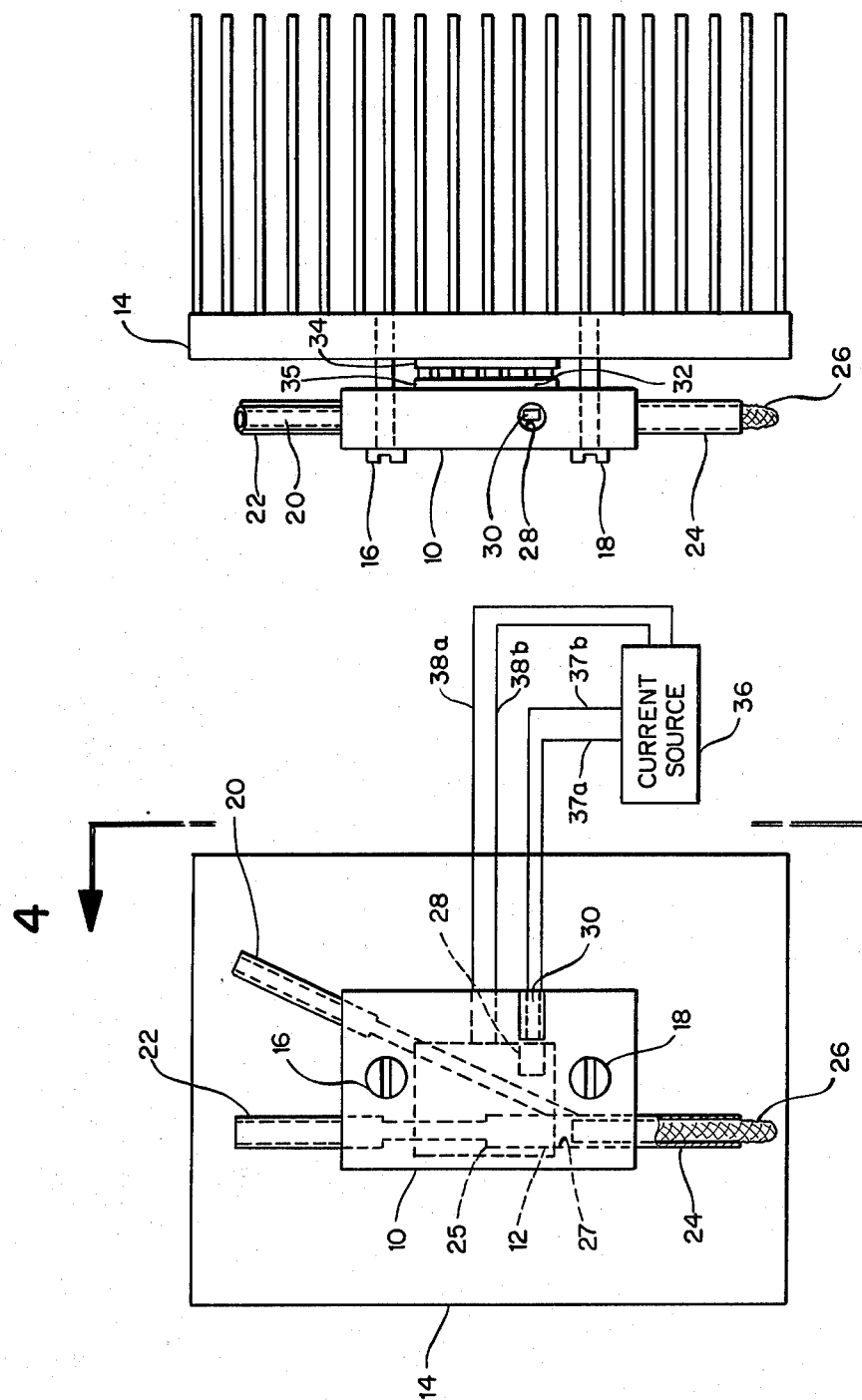
FIG. 3 is a front view of the present invention.
FIG. 4 is a side view taken along the lines 4—4 of FIG. 3.

FIG. 3 illustrates a housing 10 mounted on the surface of heat sink 14 by screws 16 and 18. Within housing 10 are three intersecting paths comprising an inlet 20 for fluid communication with a sample source (See FIG. 5), an outlet 22 for fluid communication with a sample analysis device (FIG. 5), and a drain 24 for removal of moisture from the housing 10. Inlet 20 is preferably located at an approximate 45° angle with outlet 22 and extends through a significant portion of housing 10 although any angle is permissible provided that both inlet 20 and outlet 22 are above a horizontal line traversing the intersection point. Inlet 20 is preferably of lesser diameter than outlet 22 to avoid a pressure buildup which would force a portion of the sample stream of gas to exhaust through drain 24. Inlet 20 and outlet 22 are sized for a gas flow rate within the range of 400 to 600 cubic centimeters per minute although one skilled in the art may readily alter the sizes of the preferred embodiment to accept different sample stream flow rates. In the preferred embodiment, inlet 20 is 1/16" to 3/16" in diameter and outlet 22 is $\frac{1}{8}$" to $\frac{1}{4}$" in diameter. Drain 24 may be of any suitable size although the preferred embodiment illustrates the drain as having the same diameter as counterbore 25 for ease of manufacture. Housing 10 may be manufactured of any heat conducting material although the preferred embodiment uses stainless steel to prevent corrosion from any corrosive effects of the sample gas stream which is passing through outlet 22. Disposed within drain 24 is a hygroscopic wick-like substance 26 to draw any condensed moisture out of outlet 22. In the preferred embodiment it was discovered that the top of wick 26 preferably is located in such a manner that it extends toward opening 27 to engage any condensate droplets that may settle across the opening to drain 24. Wick 26 comprises a hygroscopic fibrous material wound around a wire core in the preferred embodiment. However, wick 26 may be of any hygroscopic material having water absorbing tendency and may be as simple as a pipe cleaner or a rolled piece of paper towel. Also within housing 10 is a well 28 to accept a thermistor 30 for controlling the current flow in solid state cooling device 32 (see FIG. 4).

Referring now to FIG. 4, a side view of the present invention illustrates solid state cooling device 32 as being mounted on heat sink 14. Solid state cooling device 32 is preferably a peltier block of the type manufactured by Materials Electronic Products Corporation and may be obtained through commercial sources. Cooling device 32 is constructed to have a hot surface 34 and a cold surface 35. When current travels through cooling device 32, hot surface 34 increases in temperature and cold surface 35 decreases in temperature. Thus, the surfaces of cooling device 32 respond to changes in current flow instantaneously.

Thermistor 30 detects the temperature of housing 10 which is a function of the temperature of the sample stream of gas and varies its resistance according to the temperature of housing 10. Thermistor 30 is connected to variable current source 36. Current source 36 is connected to thermistor 30 through connector 37a and 37b and to solid state cooling device 32 through connectors 38a and 38b. Thermistor 30 detects the temperature of housing 10 and feeds this information to current source 36, which varies the current flow to solid state cooling device 32. When the temperature of housing 10 exceeds a predetermined maximum, an increased current flow is passed through solid state cooling device 32, causing an instantaneous temperature change in hot surface 34 and cold surface 35 of cooling device 32. A greater current through cooling device 32 will increase the temperature differential between hot surface 34 and cold surface 36 of cooling device 32 as indicated in the McGraw Hill Encyclopedia of Science and Technology, published by McGraw-Hill Book Company, Inc., 1971, in its description under "thermoelectricity" at page 602 of Volume 13. Since the volume necessary for cooling the temperature of the sample gas to its dew point is kept to a minimum through the use of cooling device 32, no expansion area is necessary. Prior art required an expansion area to augment cooling of the sample gas. The present invention does not require an expansion area. Thus a sample gas stream will flow through the present invention without having to fill an increase in volume at the point of cooling. Therefore, no mixing between successive increments of gas flow takes place and the gradual decrease in measured concentration of a component gas (as illustrated by curve 2B of FIG. 2) is eliminated.

Heat sink 14 is illustrated as having cooling fins to conduct the heat generated by the hot surface of solid state cooling device 32. Heat sink 14 may be of any standard design provided that it is sized to conduct the heat generated by the hot surface of electronic cooling device 32. Housing 10 is illustrated as being in close contact with cooling device 32 to promote temperature reduction in outlet 22 through conduction of heat from housing 10 to cold surface 35 of device 32. Although the drawings illustrate housing 10 as being fastened to heat sink 14 through the use of screws, any method may be used. A thermal grease is preferably used to coat the surface of solid state cooling device 32 to promote conduction between housing 10 and cold surface 35 of solid state cooling device 32 and between hot surface 34 of solid state cooling device 32 and heat sink 14.

In actual operation a sample gas stream enters inlet 20 and passes through to outlet 22. In the path comprising inlet 20 and outlet 22, the temperature of the gas stream is reduced to promote condensation of moisture. Moisture, when condensed, will travel down the walls of inlet 20 and outlet 22 to drain 24 and come in contact with wick means 26. Wick means 26 must be positioned so that it will engage and droplets of condensate which might, through surface tension, settle at the opening 27 of drain 24. Preferably wick means 26 is positioned so that its top end is near the lower portion of the inlet channel 20. The condensate will then, through the combined forces of gravity, and the hygroscopic properties of wick means 26, pass through drain 24 to outside ambience. The gas sample, entering housing 10 at a slight pressure, will be forced out through outlet 22. Wick means 26, being saturated with mositure, will greatly retard gas flow to the point of blocking any fluid communication of the sample gas between drain 24 and outside ambience while the gas stream is being passed through inlet 20 and outlet 22 thus achieving a "plugged flow" condition. A "plugged flow" condition is one wherein a sample stream of gas flows through a conduit without dilution, either from outside the conduit or within the conduit. The use of wick means 26 in combination with solid state cooling device 32 aid in producing a gas flow having concentrations resembling that of curve 2A of FIG. 2 while prior art devices produce concentration curves resembling 2B of FIG. 2 when sample gas concentrations vary according to curve 2A.

Figure 5:
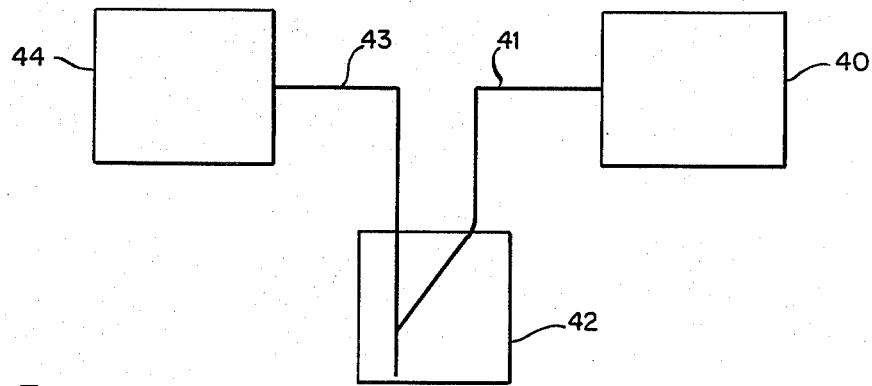
FIG. 5 is a block diagram of a gas analysis system utilizing the present invention.

FIG. 5 illustrates a block diagram of a typical system wherein the present invention is used. Sample gas source 40 is an automobile exhaust for this sample; however, source 40 may be any source which produces a sample stream of which a component gas concentration is to be measured. Source 40 is connected through inlet conduit 41 to a block representation 42 of the present invention. Block representation, or dryer, 42 is connected through exhaust conduit 43 to an analyzer 44 which is capable of measuring instantaneous concentration changes. Analyzer 44 is an oxygen analyzer in this example. However, analyzer 44 may be a carbon dioxide or carbon monoxide analyzer or any analyzer having instantaneous measurement capability.

Figure 1:
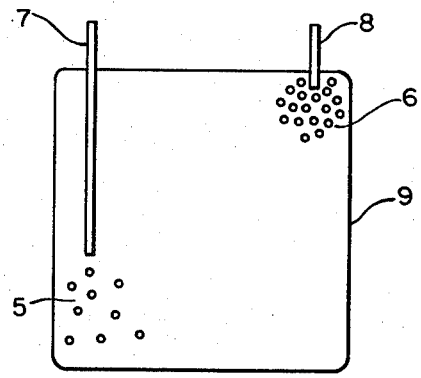
FIG. 1 illustrates a prior art moisture removal system.
Figure 2:
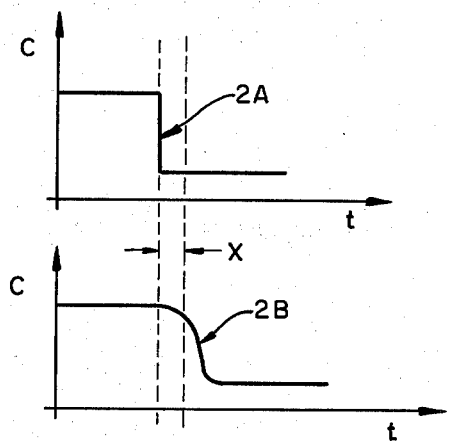
FIG. 2 is a graphical representation illustrating component gas concentration vs. time.

As illustrated in FIG. 1 and FIG. 2, a component gas concentration can change radically from one moment to the next particularly when source 40 is an automobile exhaust. FIG. 1 shows a prior art device having an inlet 7 with a gas concentration 5 and an outlet 8 with a gas concentration 6. As illustrated in FIG. 2, the gas concentration changes according to curve 2A which illustrates an instantaneous change in gas concentration. Curve 2B illustrates the gas concentration seen at exhaust 8 over a period of time. As can be seen in a comparison between curve 2A and curve 2B, an indication of the change in gas concentration on the measuring device has a time delay depicted as X. Using the prior art dryer of FIG. 1, dilution of successive increments of gas will occur in the volume necessary to cool the gas. Using the present invention gas dryer the sample gas flows from source 40 through inlet conduit 41 to dryer 42. Since dryer 42 has no expansion chamber and is quickly cooled, the component concentration of the sample stream from source 40 will not be diluted by prior increments of the sample stream and a measured concentration curve approximating that of 2A instead of that of 2B will result. Thus, the component concentration of the increment of sample stream entering the dryer through inlet conduit 41 will be the same when that increment exits dryer 42 to exhaust conduit 43 and flows to analyzer 44.

While the present invention is shown by way of the preferred embodiment, it is to be understood that the preferred embodiment is by way of illustration only and in no way limits the present invention which is to be construed only in light of the following claims.

What is claimed is:

1. An apparatus for drying a flowing sample stream of gas containing moisture, said apparatus comprising:
    housing means having three paths intersecting at a predetermined point within said housing;
    an inlet coupled to a first of said three paths to receive said sample gas stream;
    an outlet coupled to a second of said three paths to exhaust said sample gas stream;
    wick means disposed within a third of said three paths, said wick means having one end situated to absorb and transmit any condensate out of the flow of said sample gas stream;
    cooling means coupled to said housing means and responsive to temperature changes for maintaining the temperature of said housing below the dew point of said sample gas stream;
    sensor means associated with said cooling means to sense the temperature of said housing and control the heat dissipation of said cooling means.

2. The apparatus according to claim 1 wherein said wick means comprises a hygroscopic fibrous material.

3. The apparatus according to claim 1 wherein said cooling means comprises a peltier block.

4. The apparatus according to claim 1 wherein said housing means comprises a stainless steel block.

5. The apparatus of claim 1 wherein said sensor means includes a thermistor and a current source.

6. Apparatus for drying a flowing sample stream of a gas containing moisture, said apparatus comprising:
    a current source;
    a stainless steel housing having three intersecting paths comprising an inlet for receiving the sample stream, an outlet for exhausting the gas and a drain for permitting flow of moisture;
    a fibrous hydroscopic wick disposed within said drain to partially block the flow of the gas while permitting the flow of moisture;
    a peltier block connected to said current source and in contact with said stainless steel housing for lowering the temperature of the sample stream to promote separation of moisture and gas by condensation;
    a heat sink in contact with said peltier block to conduct heat to ambience; and
    a thermistor disposed within said stainless steel housing to detect the temperature of said stainless steel housing and connected to said current source to control current flow through said peltier block.

7. An apparatus for removing moisture in a sample stream of gas comprising:
    a moisture removal housing having an inlet, an outlet and a drain, the center line of the inlet intersecting the center line of the outlet at an angle of about 45°;
    solid state cooling means in contact with the moisture removal housing for reducing the temperature of the sample stream; and
    wick means disposed within the drain for drawing out any moisture which condenses out of the sample stream.

8. The apparatus of claim 7 wherein said solid state cooling means comprises a peltier block having a hot surface and a cold surface.

9. The apparatus of claim 8 also including a heat sink in contact with the hot surface of said peltier block.

10. The apparatus of claim 7 wherein said wick means comprises a fibrous hygroscopic material.

11. The apparatus of claim 7 wherein the center line of the inlet intersects the center line of the outlet at an angle of about 45°.

12. In combination:
    an analyzer for analyzing component gas concentrations in a sample stream;
    housing means for removing any moisture from said sample stream, said housing having an inlet path adapted to be connected to a source of a sample stream of gas, an outlet path connected to said analyzer and a drain path;
    wick means disposed within said drain for drawing out said moisture while partially blocking flow of said sample stream;
    solid state cooling means connected to said housing means for reducing the temperature of said sample stream to below its dew point;
    control means associated with said housing means to control current flow through said solid state cooling means, said control means varying said current in proportion to said housing temperature.

13. The combination according to claim 12 wherein said source comprises an automobile exhaust.

14. The combination according to claim 13 wherein said analyzer comprises an oxygen analyzer.

15. The combination according to claim 13 wherein said analyzer comprises a carbon monoxide analyzer.

16. The combination of claims 12, 14 or 15 wherein said solid state cooling means comprises a peltier block.

17. In an apparatus for removing moisture in a sample stream of gas in a system wherein the sample stream is passed through a moisture removal housing having an inlet, an outlet and a drain, the improvement comprising:
    solid state cooling means in contact with the moisture removal housing for reducing the temperature of the sample stream; and
    wick means comprising fibrous hygroscopic material wound around a wire core disposed within the drain for drawing out any moisture which condenses out of the sample stream.

* * * * *